United States Patent [19]

Ware et al.

[11] Patent Number: 4,462,995

[45] Date of Patent: Jul. 31, 1984

[54] PYRIDYL PHOSPHOROTHIOATE COMPOSITIONS AND THEIR USE AS ANABOLIC AGENTS

[75] Inventors: Douglas R. Ware, Riverview, Fla.; Theo A. Hymas, Midland, Mich.

[73] Assignee: The Dow Chemical Company, Midland, Mich.

[21] Appl. No.: 216,691

[22] Filed: Dec. 15, 1980

[51] Int. Cl.$^3$ ............................................ A61K 31/675
[52] U.S. Cl. .................................................... 424/200
[58] Field of Search ......................................... 424/200

[56] References Cited

U.S. PATENT DOCUMENTS 3,244,586  4/1966  Rigterink ........................... 424/200

OTHER PUBLICATIONS

Smith-J. Agr. Food Chem., pp. 132-138, vol. 15, No. 1, Jan.-Feb. 1967.
Johnson et al.-J. Dairy Science, vol. 52, No. 8, pp. 1253-1258.
Schlinke-J. of Econ. Entom., vol. 63, 1970, p. 319.
J. of Dairy Science, vol. 57, No. 12, pp. 1467-1473.

Primary Examiner—Frederick E. Waddell

[57] ABSTRACT

A method of producing an anabolic response in animals has been discovered. The method is administering an anabolically effective amount of O,O-diethyl, O-3,5,6-trichloro-2-pyridyl phosphorothioate; O,O-dimethyl, O-3,5,6-trichloro-2-pyridyl phosphorothioate; physiologically acceptable salts or combinations of the above named compounds to animals. The anabolic response produced is exhibited in one or more of the following ways:
(a) increased growth rate,
(b) increased milk production,
(c) increased protein content,
(d) improved reproductive performance,
(e) increased fiber production, and
(f) improved feed conversion efficiency in animals.

Also claimed are feed compositions containing the above named compounds.

10 Claims, No Drawings

PYRIDYL PHOSPHOROTHIOATE COMPOSITIONS AND THEIR USE AS ANABOLIC AGENTS

BACKGROUND OF THE INVENTION

1. Field of the Invention

This invention relates to a method of producing an anabolic response in animals by administering to the animals an anabolic agent whereby such response is exhibited in one or more of the following ways:

(a) increased growth rate,
(b) increased milk production,
(c) increased protein content,
(d) improved reproductive performance,
(e) increased fiber production, and
(f) improved feed conversion efficiency in animals More particularly, the present invention relates to a method of obtaining the above anabolic responses by administering to an animal an anabolically effective amount of pyridyl phosphorothioate compound from the group consisting of O,O-diethyl O-3,5,6-trichloro-2-pyridyl phosphorothioate, O,O-dimethyl, O-3,5,6-trichloro-2-pyridyl phosphorothioate or a combination thereof, hereinafter referred to as pyridyl phosphorothioate.

2. Description of the Prior Art

The use of each of chlorpyrifos, i.e., O,O-diethyl, O-3,5,6-trichloro-2-pyridyl phosphorothioate, and chlorpyrifos methyl, i.e., O,O-dimethyl, O-3,5,6-trichloro-2-pyridyl phosphorothioate, for the purpose of controlling parasites such as water pests, insects that attack plants and pests including helminths, round worms and other parasitic organisms attacking warm-blooded animals is referred to in the utility statement in the specification of U.S. Pat. No. 3,244,586. The utility statement of the patent does not describe any method of internal administration of the chlorpyrifos or chlorpyrifos methyl to warm-blooded animals for any purpose, much less any dosage rate that might be employed for the control of internal parasites. Chlorpyrifos and chlorpyrifos methyl have been administered topically on livestock for the control of ticks and lice and on household pets, such as dogs, for the control of fleas.

Heretofore, chlorpyrifos and chlorpyrifos methyl have been sold for use in the control of insects that attack valuable crops or lawns and for topical administration for use in control of insects that attack animals.

SUMMARY OF THE INVENTION

The term "anabolic response" refers to the effects exhibited by an animal in response to an anabolic agent. When an anabolic agent is administered to an animal the anabolic response is exhibited by, for example, an increase in weight gain, increase in fiber production, increase in protein content, increase in milk production in lactating animals, increase in feed conversion efficiency or improved reproductive performance when compared to animals not receiving the anabolic agent.

Improved anabolic response evidenced by one or more of increased weight gain, increased fiber production and milk production, improved reproductive performance, increased protein content, or increased feed conversion efficiency is obtained on feeding an animal selected from sheep, cattle, swine, poultry and laboratory animals such as rats and mice an anabolically effective amount of pyridyl phosphorothioate per day substantially daily for at least about 7 days and more preferably at least about 28 days. The administration of the pyridyl phosphorothioate is preferably continued even for longer periods in the case of large meat-producing animals such as cattle. Pyridyl phosphorothioate, for example, produces an anabolic response in swine when administered in an amount of from about 0.01 to about 20 milligrams per kilogram of bodyweight per day.

In commercial practice, immature sheep, cattle and swine are commonly fed for maximum growth rate in feed lots and poultry, such as chickens and turkeys, are raised in broiler pens, until they reach a marketable weight. When the desired weight of the animals is achieved, they are then sold for slaughter. It is important economically, that the animals achieve market weight in as short a time as possible, while consuming the least amount of food necessary to achieve such gain. It has been unexpectedly found that when substantially non-parasiticidal levels of pyridyl phosphorothioate specified herein are administered to animals of the classes described hereinabove, they gain weight at a faster rate while consuming less feed per pound of gain resulting in better overall economic efficiency, and reflecting the fact that administration of the pyridyl phosphorothioate results in an anabolic response.

Lactating animals exhibit an increase in milk production when administered an anabolically effective amount of the pyridyl phosphorothioate. Lactating animals seem to be more sensitive to the anabolic effects of the pyridyl phosphorothioate and thus may require a lower dose of pyridyl phosphorothioate to produce an increase in milk production when compared to an anabolically effective dose in other animals to produce an increase in body weight gain.

Animals raised for their fiber production, such as sheep, exhibit an increase in fiber production when administered an anabolically effective amount of the pyridyl phosphorothioate.

The pyridyl phosphorothioate is conveniently incorporated in a feed composition in appropriate amount to achieve the desired daily dosage in the amount of ration or supplement consumed regularly, generally about 0.5 to about 1600 grams of pyridyl phosphorothioate per ton of complete ration, depending on the age and type of animal. The pyridyl phosphorothioate may also be incorporated in a mineral, protein, or energy-type feed additive supplement in an appropriate amount to provide the above-recited daily dosage.

For commercial use, it is convenient to provide a feed additive premix or concentrate containing the pyridyl phosphorothioate in a proportion such that a predetermined quantity of the premix to be added per ton of complete ration, for example, from about 0.5 to about 1,000 pounds contains from about 0.5 to about 1600 grams of the pyridyl phosphorothioate. The feed additive premix or concentrate consists of the pyridyl phosphorothioate and a carrier such as soybean meal or ground corn or other edible feed grade material or innocuous diluent, such as alcohols, glycols or molasses, suitable for the livestock or poultry animals at hand. A concentrate may contain from about 2 to about 98 percent by weight of pyridyl phosphorothioate.

The pyridyl phosphorothioate can be administered to animals orally by dosage forms such as, in admixture with food and additionally in the form of boluses, capsules, tablets, suspensions or solutions containing the pyridyl phosphorothioate. Also, the pyridyl phosphorothioate can be administered parenterally, such as, for example, intramuscularly or intravenously, or by way of an implant which slowly releases the pyridyl phosphorothioate. The pyridyl phosphorothioate, when administered parenterally, is preferably dissolved in sterile distilled water or other physiologically acceptable liquid media and compounded in accordance with the known pharmaceutical art.

The term "feed conversion efficiency" refers to the total amount of feed consumed by an animal over a period of time divided by the gain in body weight of the animal over that period as seen in the following formula:

$$\frac{\text{feed consumed over time period}}{\text{gain in body weight over time period}}$$

The term "increased feed conversion efficiency" refers to a more efficient means of bringing animals to market weight. An increase in feed conversion efficiency will be reflected by a lower numerical value of the feed conversion efficiency number when compared to a lower feed conversion efficiency.

The term "increased protein content," when referred to as being an anabolic response, means carcass alteration of an animal exhibited by a relative increase in body protein content and a decrease in body fat content.

One of the practical effects of this invention is to bring animals such as sheep, cattle, swine and poultry promptly to market weight with minimal feed consumption. The pyridyl phosphorothioate is most conveniently dispersed uniformly throughout the normal feed or feed additive supplement of the subject animal in anabolically effective but substantially nonparasiticidal dosage levels.

While rats and mice are not ordinarily considered a meat-bearing animal, many rats and mice are now being raised for toxicology and similar industrial studies, and have been found to be a rather accurate indicator of the physiological effects of feeds and feed additives fed to larger warm-blooded animals.

The present method has been found to be advantageous when applied also to animals such as beef cattle that have received a steroid implantation, such as diethylstilbestrol, estradiol benzoate or zeralonal.

In further embodiments, the method of the present invention or compositions containing the pyridyl phosphorothioate can be advantageously employed in combination with one or more additional feed additives such as coccidiostats, antibiotics, minerals, vitamins or the like.

The animal feeds most generally used in conjunction with this invention are composed of various grain and/or grain mixtures and/or roughage feeds such as hay, cotton seed hulls, rice hulls, silage, or other high fiber feedstuffs commonly fed to meat-, milk-, and/or wool-producing animals, especially in cattle or sheep feeds. The feeds for swine, poultry and laboratory animals will consist primarily of various grain mixtures plus the usual additaments such as bran meal, soybean meal, cotton seed meal, tankage or alfalfa meals suitable for monogastric animals.

Examples of carriers for premix or concentrate compositions are soybean meal, corn oil, ground corn, barley, wheat, mineral mixtures containing, e.g., vermiculite or diatomaceous earth, corn gluten meal, corn distillers' solubles, soy flour or other modestly priced edible ingredients. The active ingredient will be in amounts to satisfy the criteria set forth above for balanced feed rations. This premix or concentrate is then in turn mixed uniformly with the normal diet for the animal as desired by the grower or the feed mixer. The above mentioned grains, grain mixtures, roughage feeds, usual additaments, carriers and innocuous diluents constitute acceptable adjuvants for purposes of this invention.

As indicated hereinabove, the amount of pyridyl phosphorothioate added to all such feeds will be in the range of about 0.5 to about 1600 grams of the pyridyl phosphorothioate per ton of feed (dry matter basis), depending on the age and type of animal. More preferably the amount of pyridyl phosphorothioate added to such feeds will be in the range of about 1 to about 700 grams per tone. Very young animals that have been weaned or young poultry one or a few days old, will have a lower feed consumption. However, as the animal goes through a growth period to a fattening period, sometimes called finishing, the feed consumption gradually increases, but generally falls in proportion to body weight.

As indicated above, the daily dosage should fall in the range of about 0.01 to about 20 milligrams per kilogram of body weight. More preferably, the dosage is in the range of about 0.3 to about 4 milligrams per kilogram of body weight, even more preferably about 0.5 to about 3 milligrams per kilogram of body weight and most preferably, about 1 to about 3 milligrams per kilogram of body weight.

Based on known information concerning the average feed intake for various sizes and types of animals, the following amounts of the pyridyl phosphorothioates are incorporated into each ton of animal feed in order to provide an anabolically effective dose of the pyridyl phosphorothioates described herein. For example, cattle on a growing diet will ordinarily be fed a diet containing from about 3 to about 800 grams pyridyl phosphorothioate per ton of feed on a dry matter basis (DM), while cattle on a fattening diet will be fed a feed containing from about 3 to about 1000 grams pyridyl phosphorothioate per ton of feed (DM). Maintenance diets fed lactating dairy cattle should contain from about 5 to about 1600 grams pyridyl phosphorothioate per ton of feed (DM), depending on the size and feed intake of animal, while non-lactating dairy cattle should receive a feed containing from about 5 to about 1000 grams pyridyl phosphorothioate per ton (DM). Lambs on dry feed will generally be fed a ration containing from about 2 to about 600 grams pyridyl phosphorothioate per tone of feed (DM). Grower pigs may be fed a ration containing from about 1 to about 400 grams pyridyl phosphorothioate per ton of feed (DM) while swine in the fattening stage will generally be supplied a ration containing from about 2 to about 500 grams pyridyl phosphorothioate per ton (DM). Poultry such as very small day-old or older birds up through starter or grower stage will generally be fed a complete ration or mash containing from about 0.5 to about 400 grams pyridyl phosphorothioate per ton of feed (DM) while poultry on a fattening diet will feed on a ration containing about 1 to about 400 grams pyridyl phosphorothioate per ton (DM).

Pyridyl phosphorothioate fed in accordance with the invention is provided to the animal at a dosage rate substantially too low to produce a parasiticidal effect.

The following examples further illustrate the practice of the present invention, but, as such, are not intended to be limitations upon the overall scope of the same.

EXAMPLE 1

A typical growing ration for ruminants is as follows:

| Ingredients | Weight Percent (D.M. Basis)** |
|---|---|
| Mixed Hay | 40.0 |
| Ground Yellow Corn | 45.0 |
| Soybean Oil Meal | 7.0 |
| Can Molasses | 7.0 |
| Dicalcium Phosphate | 0.5 |
| Trace Mineral Salt | 0.5 |
| | 100.0 |

**D.M. is dry matter basis.

In addition to the above, the following supplements are added.

| | |
|---|---|
| Vitamin A | 300 IU/lb* |
| Vitamin D | 150 IU/lb |
| Chlorpyrifos, Chlorpyrifos Methyl or a combination thereof | 3.5 to 450 grams/ton of feed |

*IU/lb is International Unit per pound.

Such a feed typically contains from about 8 to about 15 percent by weight moisture.

EXAMPLE 2

A typical finishing ration for ruminants is as follows:

| Ingredients | Weight Percent (D.M. Basis) |
|---|---|
| Ground Shelled Corn | 65.85 |
| Mixed Ground Hay | 20.00 |
| Dried Molasses | 6.00 |
| Soybean Meal | 6.00 |
| Trace Mineral Salt | 0.50 |
| Dicalcium Phosphate | 0.40 |
| Ground Limestone | 0.70 |
| | 99.45% |

In addition to the above, the following supplements are added.

| | |
|---|---|
| Vitamin A (300,000 units/gms) | 66.7 grams/ton |
| Vitamin $D_2$ (16,000,000 units/lb) | 7.1 grams/ton |
| Chlorpyrifos, Chlorpyrifos Methyl or a combination thereof | 3.5 to 450 grams/ton of feed |

Such a feed typically contains from about 8 to about 15 percent by weight moisture.

EXAMPLE 3

An example of a suitable feed additive premix is as follows:

| | |
|---|---|
| Chlorpyrifos, Chlorpyrifos Methyl or a combination thereof | 64 grams |
| Ground Yellow Corn (5-10% moisture) | 390 grams |

EXAMPLE 4

For use in the field for animals on range, the active ingredient may be administered by means of salt or molasses blocks. A typical block may be prepared using the following compositions:

| Ingredients | Weight Percent (D.M. Basis) |
|---|---|
| Dried Cane Molasses | 35.00 |
| Ground Soybean Hulls | 29.60 |
| Chlorpyrifos, Chlorpyrifos Methyl or a combination thereof* | 5.36 |
| Granulated Salt | 25.90 |
| Trace Minerals and Vitamins | 0.24 |
| Stabilized Animal Fat | 1.30 |
| Moisture | 2.60 |
| | 100.00% |

*Provided that the field animal ingests enough of the block per day to provide an effective dose of active ingredient hereinbefore mentioned.

EXAMPLE 5

If desired, the pyridyl phosphorothioate may be administered as a part of a liquid animal feed supplement such as a supplement containing a nonprotein nitrogen source such as urea in admixture with molasses and other feed ingredients. Such a liquid supplement may be prepared using the following formula:

| Ingredients | Weight Percent (D.M. Basis) |
|---|---|
| Molasses | 80.00 |
| Water | 16.25 |
| Phosphoric Acid, 85% | 2.70 |
| Urea or Ammonium Sulfate | 2.00 |
| Trace Minerals | .50 |
| Vitamin A, D & E | .05 |
| Salt | 1.00 |
| Chlorpyrifos, Chlorpyrifos Methyl or a combination thereof* | .20 |
| | 100.00% |

*Provided the animal drinks enough of the liquid per day to provide an effective dose of active ingredient hereinbefore mentioned.

The following examples demonstrate the anabolic effects of pyridyl phosphorothioate as seen by an increase in the average daily gain in pounds, increased feed conversion efficiency or increased milk production.

EXAMPLE 6

Eighteen (18) young growing cattle were alloted to 6 treatment groups of 3 animals each. Chlorpyrifos, in the following dosages, was fed to the animals by incorporation into the feed. The test was carried on for 30 days. Treatment 1, 0 mg/kg, served as the control group. The results are tabulated as follows:

| Treatment | Dosage, mg/kg/day | Average Daily Gain, lbs. |
|---|---|---|
| 1 | 0 | 0.96 |
| 2 | 0.1 | 1.71 |
| 3 | 0.3 | 0.79 |
| 4 | 1.0 | 0.93 |
| 5 | 3.0 | 1.14 |
| 6 | 3.0 | 1.89 |

The average daily gain of all of the treatment groups was 1.29 as compared to the control group which was 0.96.

EXAMPLE 7

Eighteen (18) young growing swine were allotted into 4 treatment groups with 3 animals in each treatment group except treatment group 4 which had 9 animals. Chlorpyrifos, in the following dosages, was fed to the animals by incorporation into the feed. The test was conducted for 30 days. The results are tabulated as follows:

| Treatment | Dosage mg/kg/day | Average Daily Feed, lbs. | Average Daily Gain, lbs. | Feed Conversion Efficiency, lb Feed/lb Weight Gain |
|---|---|---|---|---|
| 1 | 0 | 4.40 | 1.50 | 2.93 |
| 2 | .05 | 4.10 | 1.50 | 2.73 |
| 3 | .15 | 4.50 | 1.57 | 2.87 |
| 4 | .50 | 4.57 | 1.69 | 2.70 |

EXAMPLE 8

Eighty (80) young growing rats were allotted into 4 treatment groups with 10 animals of each sex in each treatment group. Chlorpyrifos, in the following dosages, was fed to the animals by incorporation into the feed. The test was conducted for 90 days. The results are tabulated as follows:

| Treatment | Dosage (mg/kq/day) | Average Body Weight, grams (g) | | Daily Feed Consumption, g | |
|---|---|---|---|---|---|
| | | Males | Females | Males | Females |
| 1 | 0 | 287 | 192 | 22 | 20 |
| 2 | 1 | 338 | 194 | 24 | 21 |
| 3 | 3 | 330 | 202 | 23 | 23 |
| 4 | 10 | 290 | 198 | 25 | 26 |
| 5 | 30 | 267 | 170 | 29 | 24 |
| 6 | 100 | (NOT AVAILABLE) | | 14 | 13 |

EXAMPLE 9

Three hundred (300) young growing rats were allotted into 6 treatment groups with 25 animals of each sex in each treatment group. Chlorpyrifos, in the following dosages, was fed to the animals by incorporation into the feed. The test was conducted for 14 months. The results are tabulated as follows:

| Treatment | Dosage (mq/kq/day) | Average Body Weight, g | | Daily Feed Consumption, g | |
|---|---|---|---|---|---|
| | | Males | Females | Males | Females |
| 1 | 0 | 460 | 305 | 26 | 20 |
| 2 | .01 | 475 | 310 | 25 | 19 |
| 3 | .03 | 474 | 320 | 24 | 21 |
| 4 | .10 | 474 | 310 | 25 | 19 |
| 5 | 1.0 | 492 | 332 | 25 | 22 |
| 6 | 3.0 | 485 | 330 | 25 | 21 |

EXAMPLE 10

Twenty-four (24) young growing swine were allotted into 6 treatment groups with 3 animals in each group. Chlorpyrifos methyl, in the following dosages, was fed to the animals by incorporation into the feed for 30 days. The results are tabulated as follows:

| Treatment | Dosage mg/kg/day | Average Daily Gain, kg | Feed Conversion Efficiency |
|---|---|---|---|
| 1 | 0 | .59 | 3.22 |
| 2 | .04 | .64 | 3.11 |
| 3 | .12 | .78 | 2.89 |
| 4 | .40 | .72 | 3.24 |
| 5 | 1.20 | .67 | 3.45 |
| 6 | 4.0 | .57 | 3.92 |
| 7 | 4.0 | .64 | 3.37 |
| 8 | 4.0 | .88 | 3.01 |

When administered to animals at a dosage of from about 0.01 to about 20 mg/kg/day, each of chlorpyrifos, chlorpyrifos methyl or a combination thereof, the utility of which is not specifically exemplified above, has the ability to achieve one or more of the hereinabove listed anabolic responses in said animals.

Starting Materials

The present pyridyl phosphorothioate compounds are known compounds and their preparation is taught in U.S. Pat. No. 3,244,586.

What is claimed is:

1. A method of increasing the growth rate and/or improving the feed conversion efficiency in ruminants and swine which comprises administering to said ruminant or swine an effective amount of from about 0.3 to about 4 milligrams per kilogram of bodyweight per day of a pyridyl phosphorothioate compound from the group consisting of O,O-diethyl, O-3,5,6-trichloro-2-pyridyl phosphorothioate; O,O-dimethyl, O-3,5,6-trichloro-2-pyridyl phosphorothioate; or a physiologically acceptable salt thereof or a combination thereof.

2. The method of claim 1 wherein said compound O,O-diethyl, O-3,5,6-trichloro-2-pyridyl phosphorothioate or a physiologically acceptable salt thereof.

3. The method of claim 1 wherein said compound is O,O-dimethyl, O-3,5,6-trichloro-2-pyridyl phosphorothioate or a physiologically acceptable salt thereof.

4. The method of claim 1 wherein said compound is administered orally.

5. The method of claim 1 wherein said compound is administered on a substantially daily basis.

6. The method of claim 1 wherein said compound is administered for at least 7 days.

7. The method of claim 1 wherein said anabolically effective amount is from about 0.5 to about 3 milligrams per kilogram of bodyweight per day.

8. The method of claim 1 wherein said anabolically effective amount is from about 1 to about 3 milligrams per kilogram of bodyweight per day.

9. The method of claim 1 wherein said compound is in admixture with an adjuvant.

10. The method of claim 8 wherein said compound is O,O-diethyl, O-3,5,6-trichloro-2-pyridyl phosphorothioate or a physiologically acceptable salt thereof.

* * * * *

UNITED STATES PATENT AND TRADEMARK OFFICE
CERTIFICATE OF CORRECTION

PATENT NO. : 4,462,995
DATED : July 31, 1984
INVENTOR(S) : Douglas R. Ware and Theo A. Hymas It is certified that error appears in the above-identified patent and that said Letters Patent are hereby corrected as shown below:

Column 4, line 13, "grams per tone." should read -- grams per ton. --.

Column 4, line 50, "per tone of feed" should read -- per ton of feed --.

Column 5, line 11, Example 1, "Can Molasses" should read -- Cane Molasses --.

Column 7, line 31, Example 8, "Weiqht,grams(g)" should read -- Weight,grams(g) --.

Column 7, line 32, Example 8, "(mg/kq/day)" should read -- (mg/kg/day) --.

Column 7, line 51, Example 9, "(mq/kq/day)" should read -- (mg/kg/day) --.

Column 8, line 39, "said compound" should read -- said compound is --.

Signed and Sealed this

Seventh Day of May 1985

[SEAL]

Attest:

DONALD J. QUIGG

Attesting Officer       Acting Commissioner of Patents and Trademarks